(12) United States Patent
Shenoy et al.

(10) Patent No.: US 8,294,007 B2
(45) Date of Patent: Oct. 23, 2012

(54) METHOD OF STABILIZATION OF FUNCTIONAL NANOSCALE PORES FOR DEVICE APPLICATIONS

(75) Inventors: Devanand K. Shenoy, McLean, VA (US); Alok Singh, Springfield, VA (US); William R. Barger, Cobb Island, MD (US); John J. Kasianowicz, Darnestown, MD (US)

(73) Assignees: The United States of America, as represented by the Secretary of the Navy, Washington, DC (US); The United States of America, as represented by the Secretary of Commerce, Washington, DC (US)

( * ) Notice: Subject to any disclaimer, the term of this patent is extended or adjusted under 35 U.S.C. 154(b) by 1921 days.

(21) Appl. No.: 11/070,398

(22) Filed: Feb. 28, 2005

(65) Prior Publication Data

US 2005/0191616 A1 Sep. 1, 2005

Related U.S. Application Data

(60) Provisional application No. 60/550,739, filed on Mar. 1, 2004, provisional application No. 60/559,288, filed on Mar. 31, 2004.

(51) Int. Cl.
*B05D 1/28* (2006.01)
(52) U.S. Cl. ......... 977/713; 977/714; 977/783; 977/849
(58) Field of Classification Search ............... 216/2, 39, 216/56, 57, 79, 99; 560/231, 205
See application file for complete search history.

(56) References Cited

U.S. PATENT DOCUMENTS

| 5,516,890 A | 5/1996 | Tomich |
| 6,362,002 B1 | 3/2002 | Denison |
| 6,428,959 B1 | 8/2002 | Deamer |

OTHER PUBLICATIONS

Sugao et al. Na/D-Glucose Cptransporter Based Bilayer Lipid Membrane Sensor for D-Glucose, Anal. Chem. 1993, 65, 363-369.*
United States Statutory Invention Registration No. H201.*
Toxicon (1972), 70(5), 501-9.*
Nature (London) (1997), 385(6619), 833-838.*
Biochimica et Biophysica Acta, Biomembranes (1980), 602(1), 57-69.*
Israel Journal of Chemistry (1980), Volume Date 1979, 18(3-4), 325-9.*
Biochimica et Biophysica Acta, Biomembranes (1982), 687(2), 165-9.*
Kennedy et al., Science, New Series, 196 (4296), 1977 pp. 1341-1342.*
Silvermann et al., J. Biol. Chem. 269(36) 1994 pp. 22524-22532.*
Knoll et al., Reviews in Molecular Biotechnology 74(2000) 137-158.*

(Continued)

*Primary Examiner* — Karl J Puttlitz
(74) *Attorney, Agent, or Firm* — Amy L. Ressing; Joseph T. Grunkemeyer

(57) ABSTRACT

A membrane is disclosed made from a compound having a hydrophilic head group, an aliphatic tail group, and a polymerizable functional group. The membrane spans an aperture and may be polymerized. The membrane may be useful for DNA sequencing when the membrane includes an ion channel.

23 Claims, 10 Drawing Sheets

OTHER PUBLICATIONS

Henrickson, "Driven DNA Transport into an Asymmetric Nanometer-Scale Pore" Phys. Rev. Lett., 85(14), p. 3057-60 (Oct. 2000).

Fyles, "Activities and Modes of Action on Artificial Ion Channel Mimics" J. Am. Chem. Soc., 1993, 115, 12315-21.

Tanaka, "Photochemical regulation of ion channel transport through 'quasi-channels' embedded in black lipid membrane" Mat. Sci. and Eng. C, 4 (1997) 297-301.

Kasianowicz, "Characterization of individual polynucleotide molecules using a membrane channel" Proc. Nat. Acad. Sci, 93, 13770-3 (Nov. 1996).

Montal, "Formation of Bimolecular Membranes from Lipid Monolayers and a Study of Their Electrical Properties" Proc. Nat. Acad. Sci, 69(12), 3561-6 (Dec. 1972).

Kasianowicz, "Simultaneous Multianalyte Detection with a Nanometer-Scale Pore" Anal. Chem. 73, 2268-72 (2001).

* cited by examiner

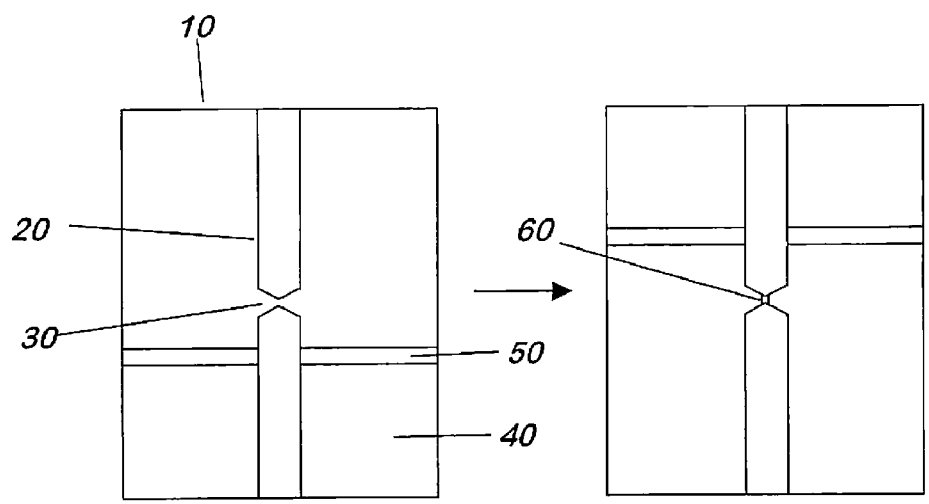
FIG. 3(a)  FIG. 3(b)
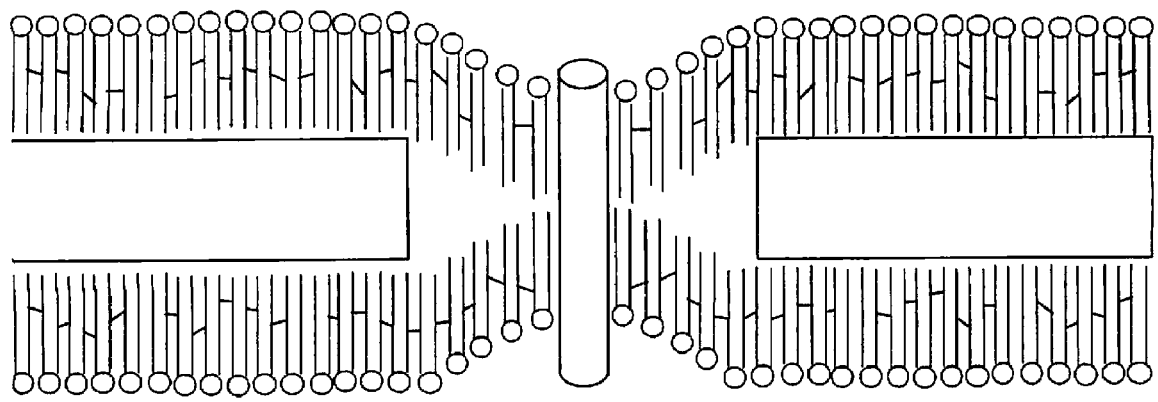
FIG. 4

METHOD OF STABILIZATION OF FUNCTIONAL NANOSCALE PORES FOR DEVICE APPLICATIONS

This application claims priority to U.S. Provisional Patent Application No. 60/550,739 filed on Mar. 1, 2004 and to U.S. Provisional Patent Application No. 60/559,288 filed on Mar. 31, 2004, both incorporated herein by reference.

BACKGROUND OF THE INVENTION

1. Field of the Invention

The present invention relates generally to lipid membranes.

2. Description of Related Art

Protein pores, such as alpha-Hemolysin, have been shown to act as stochastic sensors for a wide range of target molecules. A protein pore is used to reconstitute a planar phospholipid bilayer membrane. A black lipid membrane (BLM) is formed on a thin Teflon partition with a hole in the middle several tens of microns in diameter. The partition separates identical aqueous media (e.g. 1 M KCl with buffer at neutral pH) in a trough. A voltage is applied so as to drive an ionic current through the open pore. If single stranded DNA is introduced into the cis chamber (the chamber with the negative electrode) current blockades are observed during polyanionic DNA translocation through the protein pore into the opposite trans chamber. (Henrickson et al., "Driven DNA Transport into an Asymmetric Nanometer-Scale Pore," *Phys. Rev. Lett.*, 85, 3057 (2000). All referenced publications and patent documents are incorporated herein by reference.) The bilayer membrane in these studies is made of non-polymerizable phospholipids. Experiments designed to study protein channels in such lipids typically last only a few hours after which the membrane becomes unstable.

Protein ionic channels in planar lipid bilayer membranes permit the study of ion and macromolecular transport through single or multiple nanometer-scale pores. Nearly four decades since this in vitro system was developed liquid-crystalline membranes limit the use of protein nanopores for real-world applications because of the weak intermolecular interactions that stabilize phospholipid membranes.

Ion channels provide the molecular basis for nerve activity and mediate the selective transport of ions and macromolecules. In addition, some ion channels connect cells together to form large-scale functioning tissue whereas others act as lethal toxins. It has been shown that channels could act as components of sensors to detect a variety of analytes including ions and small molecules polynucleotides, and proteins. Black lipid membranes (BLMs), phospholipid bilayers that span small apertures, have provided a convenient platform for most of these studies. However, conventional planar lipid bilayer membranes are too fragile to be used in analytical applications and for long-term studies of ion channels.

SUMMARY OF THE INVENTION

The invention comprises a structure comprising a membrane of a compound spanning an aperture. The compound comprises a hydrophilic head group, an aliphatic tail group, and a polymerizable or polymerized functional group.

The invention further comprises a method of forming a structure comprising: providing a solution of a compound and a chamber comprising a partition having an aperture; placing a quantity of an aqueous liquid into the chamber, such that the liquid does not cover any part of the aperture; placing the solution on the top surface of the liquid; and raising the solution to a point above the aperture to form a membrane of the compound across the aperture. The compound comprises a hydrophilic head group and an aliphatic tail group and comprises a polymerizable functional group in an organic solvent

BRIEF DESCRIPTION OF THE DRAWINGS

A more complete appreciation of the invention will be readily obtained by reference to the following Description of the Example Embodiments and the accompanying drawings.

FIG. 3 schematically illustrates a method for forming a membrane across an aperture.

FIG. 4 schematically illustrates an ion channel in a bilayer membrane.

DETAILED DESCRIPTION OF THE EXAMPLE EMBODIMENTS

Figure 1:
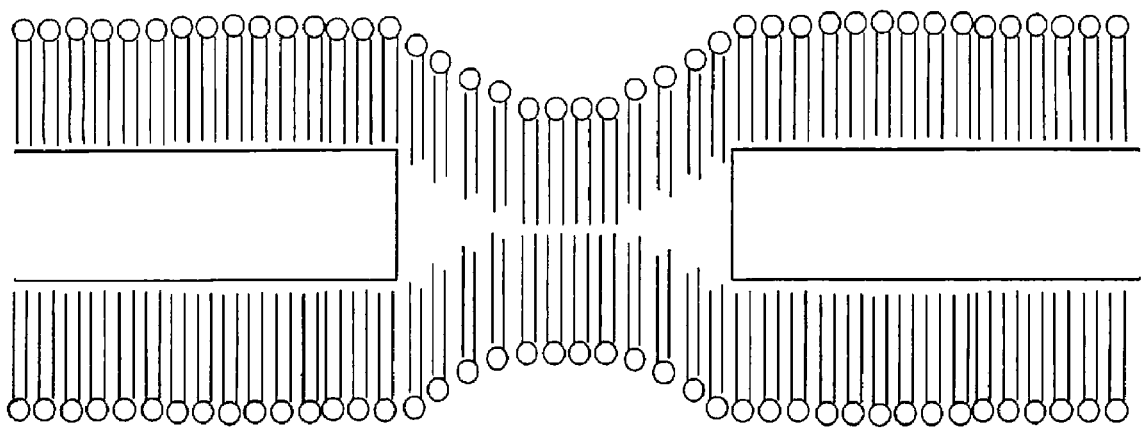
FIG. 1 schematically illustrates a bilayer membrane spanning an aperture in a solid surface.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The invention may be useful to immobilize functional protein channels in planar lipid membranes. Specifically, the approach may enable high selectivity, sensitivity, and real-time molecular recognition for a variety of target small molecules and macromolecules of interest such as DNA and RNA. The approach may provide a means to stabilize channels of interest for applications such as DNA and RNA sequencing of pathogens, for example.

To reduce the problems associated with instability, the method disclosed here describes a means to immobilize protein pores within a polymerizable lipid membrane. The protein pore may remain functional before and after polymerization. The ease of forming bilayer membranes can be correlated with the elasticity of the membrane, derived from Langmuir Blodgett isotherms.

Two types of polymerizable lipids may form planar membranes and permit functional reconstitution of protein ion channels formed by *Staphylococcus aureus* α-hemolysin (αHL) and *Bacillus anthracis* protective antigen 63. Single-stranded DNA can be driven through the αHL channel in non-polymerizable phospholipid membranes. This is also the case for αHL in polymerizable membranes both before and after the membrane is polymerized. Surface pressure measurements suggest that the ease of forming membranes may depend on the surface elasticity estimated from Langmuir-Blodgett monolayer pressure-area isotherms. Polymerizable lipids may ultimately permit locking channels in ultra-thin films for a wide variety of biotechnological and analytical applications.

A possible advantage of this approach is that experiments on protein channels may now be performed over extended periods of time—perhaps months to years. Once polymerized, the membrane and channel may remain functional for a long time. This allows an opportunity to do basic research on such channels, for example, observing the time-dependent properties of such channels and pores. A second possible advantage is that device applications utilizing protein pores may become possible. One of the device applications is the use of protein pores as stochastic sensors. Earlier work has clearly demonstrated that alpha-Hemolysin pores either as wild type or in an engineered form can be used to detect a wide variety of chemical and biological targets for defense and civilian applications (e.g. drug industry). There is now an opportunity to immobilize such pores in a robust manner for long-term applications.

membrane may also contain one or more of the compounds along with other similar materials that do not contain a polymerizable or polymerized functional group, such as non-polymerizable lipids.

The membrane may occur in two forms: a single layer membrane or a bilayer membrane. The bilayer membrane has the typical morphology of lipid bilayer membranes, that is, a majority to substantially all of the head groups is on the surfaces of the membrane, and a majority to substantially all of the tail groups is in the interior of the membrane. In the bilayer membrane, the functional group is in the tail group. The compound may have two tail groups, only one of which has a functional group.

A suitable functional group in the bilayer embodiment is a diacetylene or polymerized diacetylene group. Suitable head groups in the bilayer embodiment include, but are not limited to, phosphoethanolamine ($NH_3^+C_2H_4PO_4^-$) and phosphocholine ($N(CH_3)_3^+C_2H_4PO_4^-$). Suitable compounds include, but are not limited to, 1-palmitoyl-2-tricosadiynoyl-glycero-3-phosphoethanolamine having a diacetylene group in the tricosadiynoyl group and stereoisomers thereof, such as 1-palmitoyl-2-tricosadiynoyl-sn-glycero-3-phosphoethanolamine having a diacetylene group in the tricosadiynoyl group. A suitable example is 1-palmitoyl-2-10,12-tricosadiynoyl-glycero-3-phosphoethanolamine and stereoisomers thereof, such as 1-palmitoyl-2-10,12-tricosadiynoyl-sn-glycero-3-phosphoethanolamine (PTPE), shown in Eq. (1). Another possible compound is 1,2-bis(tricosa-10,12-diynoyl)-glycero-3-phosphocholine or 1,2-bis(tricosa-10,12-diynoyl)-sn-glycero-3-phosphocholine ($DC_{8,9}PC$), shown in Eq. (2), though this compound may be inferior to PTPE.

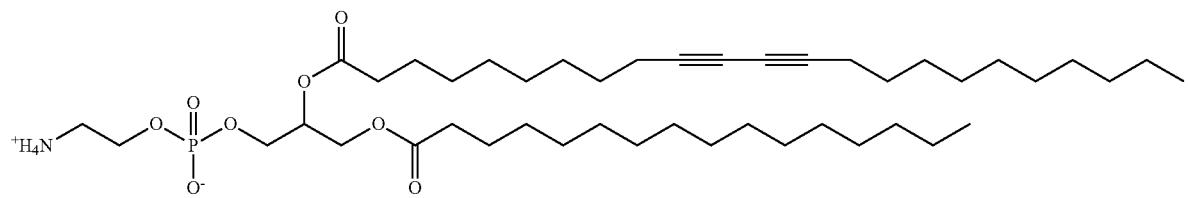

(1)

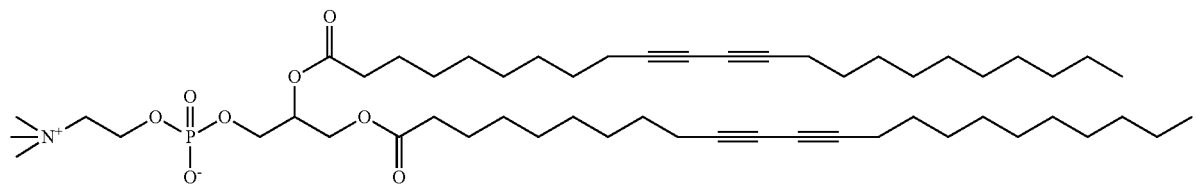

(2)

All embodiments of the invention include a membrane of a compound. The compound comprises a hydrophilic head group and an aliphatic tail group, such as a lipid. The compound also comprises a polymerizable or polymerized functional group. The functional group may be part of either the head group or the tail group.

A variety of such compounds may be used. The tail group may comprise an ester group bonding the tail group to the head group. The compound may comprise two tail groups bound to one head group. Suitable tail groups include, but are not limited to, saturated or unsaturated $C_{11}$-$C_{24}$ aliphatic groups.

A single compound may be used or combinations of different compounds may be used in a single membrane. A The mechanism of UV-induced polymerization in diacetylenic phospholipids is known. The triple bonds in the hydrocarbon chains (e.g., in PTPE) are replaced with double bonds with hydrocarbon chains of adjacent molecules. This may cause a change in the membrane dielectric constant and thus the membrane capacitance. However, the capacitance is inversely proportional to the film thickness. Thus, the UV-induced increase in PTPE membrane capacitance, $C_m$, is probably due to a decrease in the membrane thickness. If this effect arises solely from a tilt of the PTPE molecules, then a 20% increase in $C_m$ would correspond to a 36 degree tilt in the lipid hydrocarbon tails, assuming that the lipids are rigid rods and their long axis is initially oriented perpendicular to the plane of a 4 nm thick membrane.

Compounds may be screened for their suitability in the bilayer membrane by determining the surface compressional modulus in a Langmuir-Blodgett (LB) film. Methods for measuring this modulus are disclosed herein. A modulus of about 50 to about 150 mN/m may have the proper elasticity to form a stable black lipid membrane, though the invention is not limited to this range. PTPE has a modulus of about 105 mN/m and $DC_{8,9}PC$ has a modulus of about 300 mN/m.

Figure 6:
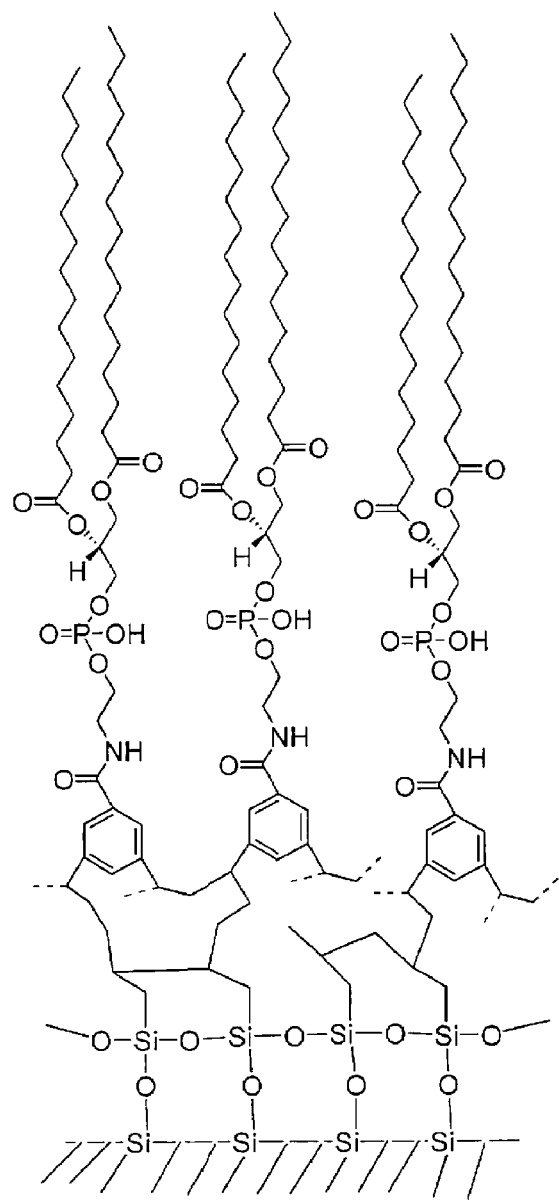
FIG. 6 shows a head-polymerized compound bound to a silanized surface.
Figure 7:
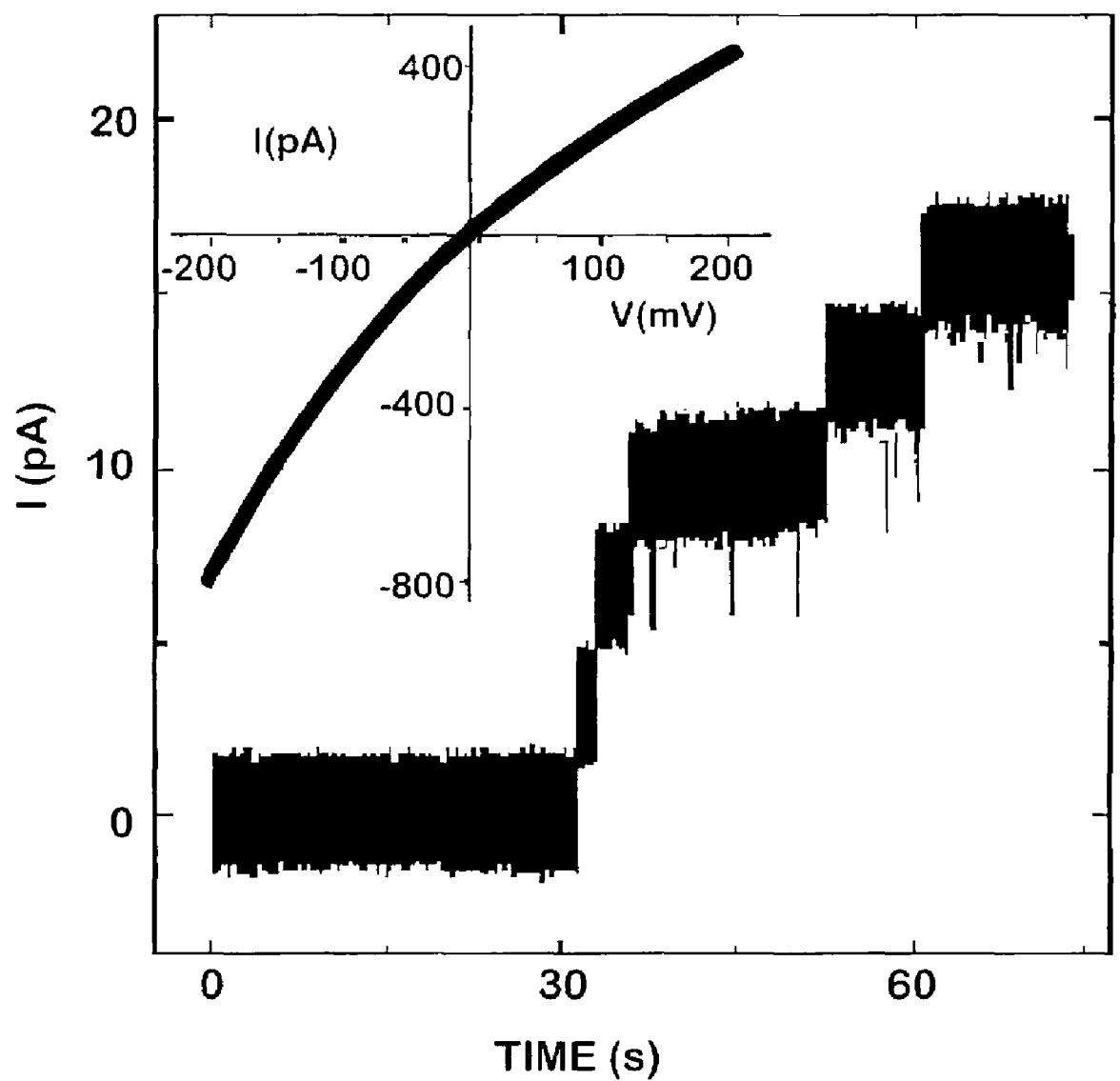
FIG. 7 illustrates the current-voltage relationship for a PTPE bilayer membrane with PA63.

In another embodiment, the membrane is a single layer membrane on a solid surface. The head groups comprise the functional group, are oriented towards a substrate, and may be covalently bound to the substrate. Suitable functional groups include, but are not limited to, polymerized or nonpolymerized phospho-N-(2-hydroxymethyl)-3,5-divinylbenzamide $(C_6H_3(CH_2CH)_2CONHC_2H_4PO_4^-—)$. Suitable compounds include, but are not limited to, 1,2-dipalmitoyl-glycero-3-phospho-N-(2-hydroxymethyl)-3,5-divinylbenzamide and 1,2-dipalmitoyl-sn-glycero-3-phospho-N-(2-hydroxymethyl)-3,5-divinylbenzamide (DPPE-DVBA), shown in Eq. (3).

limited to, diacetylene and divinylbenzamide may be polymerized by exposure to UV radiation. An advantage of UV exposure is that it does not physically disturb the membrane. The polymerization forms crosslinks between either tail groups or head groups. FIG. 6 shows a polymerized divinylbenzamide head group bound to a silanized substrate.

Three criteria may be used to confirm that the polymerizable lipids formed planar membranes. First, the capacitively coupled current may increase by an amount expected when the membrane is formed. Second, the membranes may be ruptured by applying potentials with magnitudes >>200 mV. Third, the subsequent addition of several pore-forming channels to the aqueous phase bathing one side of the membrane may cause spontaneous ion channel formation.

Figure 5:
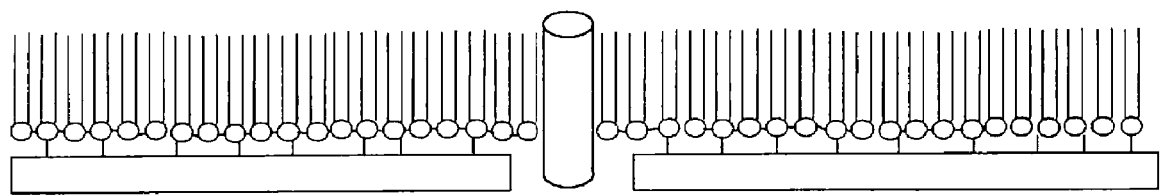
FIG. 5 schematically illustrates an ion channel in a single layer membrane.

Optionally, an ion channel may be incorporated into the membrane. FIGS. 4 and 5 schematically illustrate this arrangement in bilayer and single layer membrane, respectively. The ion channel can form a pore all the way through the membrane. This may be done either before or after the functional group is polymerized. The pore can be a protein ion

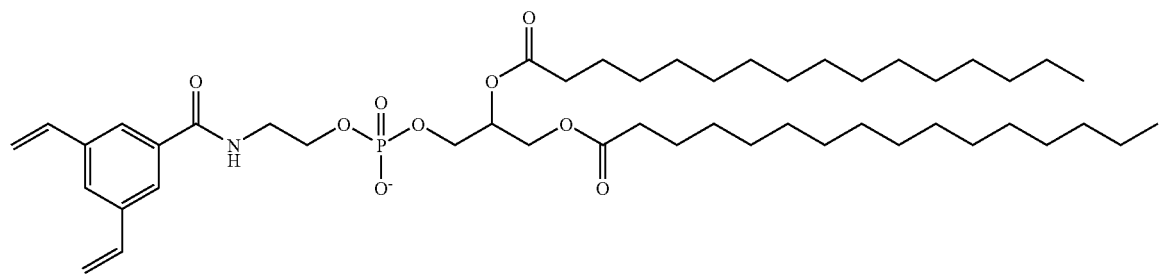

(3)

Figure 2:
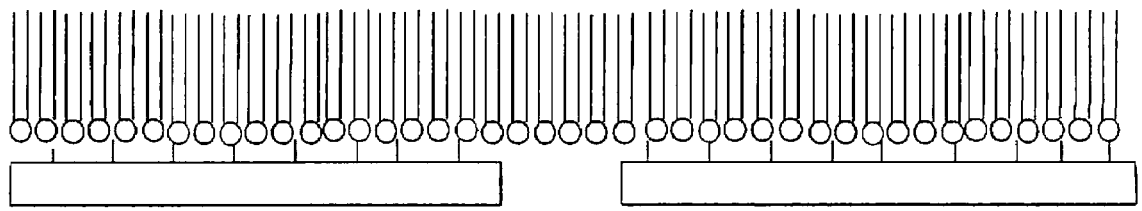
FIG. 2 schematically illustrates a single membrane bound to a solid surface and spanning an aperture in the surface.

In both embodiments, the membrane spans an aperture in a surface, such as in a black lipid membrane. The membrane completely covers the aperture and is in contact with the surface all the way around the aperture. FIG. 1 schematically illustrates a bilayer membrane spanning an aperture in a solid surface. The area between the two layers and the substrate is an annulus containing trapped solvent. FIG. 2 schematically illustrates a single layer membrane bound to a solid surface and spanning an aperture in the surface. Both membranes are shown as not crosslinked.

A suitable method for preparing such a membrane spanning an aperture is schematically illustrated in FIG. 3. A quantity of aqueous fluid 40, such as an electrolyte, is placed into a chamber 10, containing a partition 20 having an aperture 30. The aperture may be much smaller than shown, typically from about 2 nm to about 250 microns or from about 10 microns to about 100 microns in diameter. The liquid does not cover any part of the aperture as shown in FIG. 3(a). A solution 50 of the compound is provided. The functional group in the compound is a polymerizable functional group. The solution may be an organic solution, such that the solution is immiscible with water. The solution is placed on top of the liquid as shown in FIG. 3(a). The solution is then raised to a point above the aperture as shown in FIG. 3(b). This may be done, for example, by raising the bottom of the chamber, lowering the partition, tilting the chamber, or by adding more aqueous liquid below the solution. As the solution covers the aperture, the compound self-assembles into a membrane 60. The membrane may be surrounded by the aqueous liquid on both sides.

Once the membrane is formed, the functional group may be polymerized. Certain functional groups including, but not channel. Protein ion channels are typically naturally occurring proteins with a biological function. They may by produced by bacteria. Suitable protein ion channels include, but are not limited to, *Staphylococcus aureus* alpha-hemolysin, *Bacillus anthracis* protective antigen 63, and gramicidin.

The ion channel may also be a synthetic, or non-naturally occurring compound. Suitable ion channels are disclosed in Shenoy et al., U.S. patent application Ser. No. 11/070,397 (incorporated herein by reference).

The polymerized membrane with ion channel may remain stable for extending periods of time, including indefinitely. Without polymerization, the membrane could quickly lose its structure.

The entire structure including the polymerized membrane, aperture, and ion channel may be useful for DNA and other polynucleotide sequencing. An electrolyte solution containing the DNA is place on one side of the membrane. Electrolyte is also placed on the other side of the membrane. A voltage is applied through the electrolytes and across the membrane. This causes a DNA strand to gradually pass through the membrane. As the strand passes through, the current passing through the membrane is measured. The current is affected by the number and identity of the nucleotides presently in the pore. When using protein ion channels, there is typically more than one nucleotide in the pore. The identity of each nucleotide is determined from several current measurements as the nucleotide passes through the pore. A synthetic pore may be short enough to hold only one nucleotide. This simplifies the sequencing, as each nucleotide identification is determined from a single current measurement.

Having described the invention, the following examples are given to illustrate specific applications of the invention.

These specific examples are not intended to limit the scope of the invention described in this application.

EXAMPLE 1

Formation of folded bilayer—All experiments were performed at room temperature, i.e., (22.5±1)° C. All of the lipids were purchased from Avanti Polar Lipids (Alabaster, Ala.). $DC_{8,9}PC$ was in chloroform at either 2 mg/mL or 10 mg/mL (w/v). PTPE was in benzene at 10 mg/mL (w/v), and the nonpolymerizable DiPhyPC was in pentane or benzene at 10 mg/mL (w/v). Lipid bilayer membranes were formed in a polytetrafluoroethylene (PTFE) chamber using a variation of a technique devised by Montal et al., "Formation of bimolecular membranes from lipid monolayers and a study of their electrical properties," *Proc. Natl. Acad. Sci.* (*USA*), 69, 3561-3566 (1972). Briefly, membranes were formed across 80 μm to 100 μm diameter holes in a PTFE film partition (25 μm thick) that divided the chamber in two halves. Initially, aqueous electrolyte solution partially filled each half of the chamber (volume: 2 mL; surface area: ~1 $cm^2$). Fifteen or more microliters of lipid suspended in a volatile organic solvent was applied at the air-electrolyte solution interface when the electrolyte levels were well below the hole in the partition. The electrolyte levels were raised sequentially to a point just above the hole to form the membrane. The process was monitored visually with a microscope and electronically by measurements of the capacitively coupled current. Prior to raising the electrolyte levels, the rim of the hole was coated with hexadecane using a solution of hexadecane in pentane (1:100 v/v). Ag/AgCl electrodes (In-Vivo Metrics, Healdsburg, Calif.) were used to apply the voltage across the partition and membrane.

EXAMPLE 2

Langmuir Blodgett films—The surface pressures of monolayers for each lipid ($DC_{8,9}PC$, PTPE and diphytanoylphosphatidylcholine (DiPhyPC)) were determined at 22° C. with a NIMA Model 611 MC Langmuir-Blodgett trough using the Wilhelmy plate method. The monolayers were spread from chloroform solutions (~0.452 to 0.550 mg/mL lipid/ $CHCl_3$, w/v) at an 85 $cm^2$ air-water interface. After waiting 10 min for the chloroform to evaporate, the surface pressure was measured continuously as the monolayer trough barriers were compressed at 5 $cm^2$/min.

EXAMPLE 3

Polymerization of lipids—For polymerization at the air-water interface, a few microliters of a solution of PTPE in chloroform were spread at the air-water interface. The film was then compressed to a surface pressure of ~31 mN/m. The film was then exposed to 254 nm radiation from a UVP lamp (UVP, M/N UVS-28, rated at ~1 mW/$cm^2$ at 7.6 cm) that was held ~13 cm from closest point of the film surface.

To determine whether the planar bilayer membranes could be polymerized and remain functional, PTPE BLMs were formed and subsequently illuminated with UV light from a pen ray lamp (UVP Light Sources, Upland, Calif., M/N 11SC-2, rated at 1.9 mW/$cm^2$ at 1.9 cm, held at 2 cm from the sample). Within several minutes, lipids in the chamber changed from transparent to a vivid orange color, which suggests that some of the diynes in the hydrocarbon chains covalently linked to similar entities within nearest neighbor lipid molecules.

Figure 8:
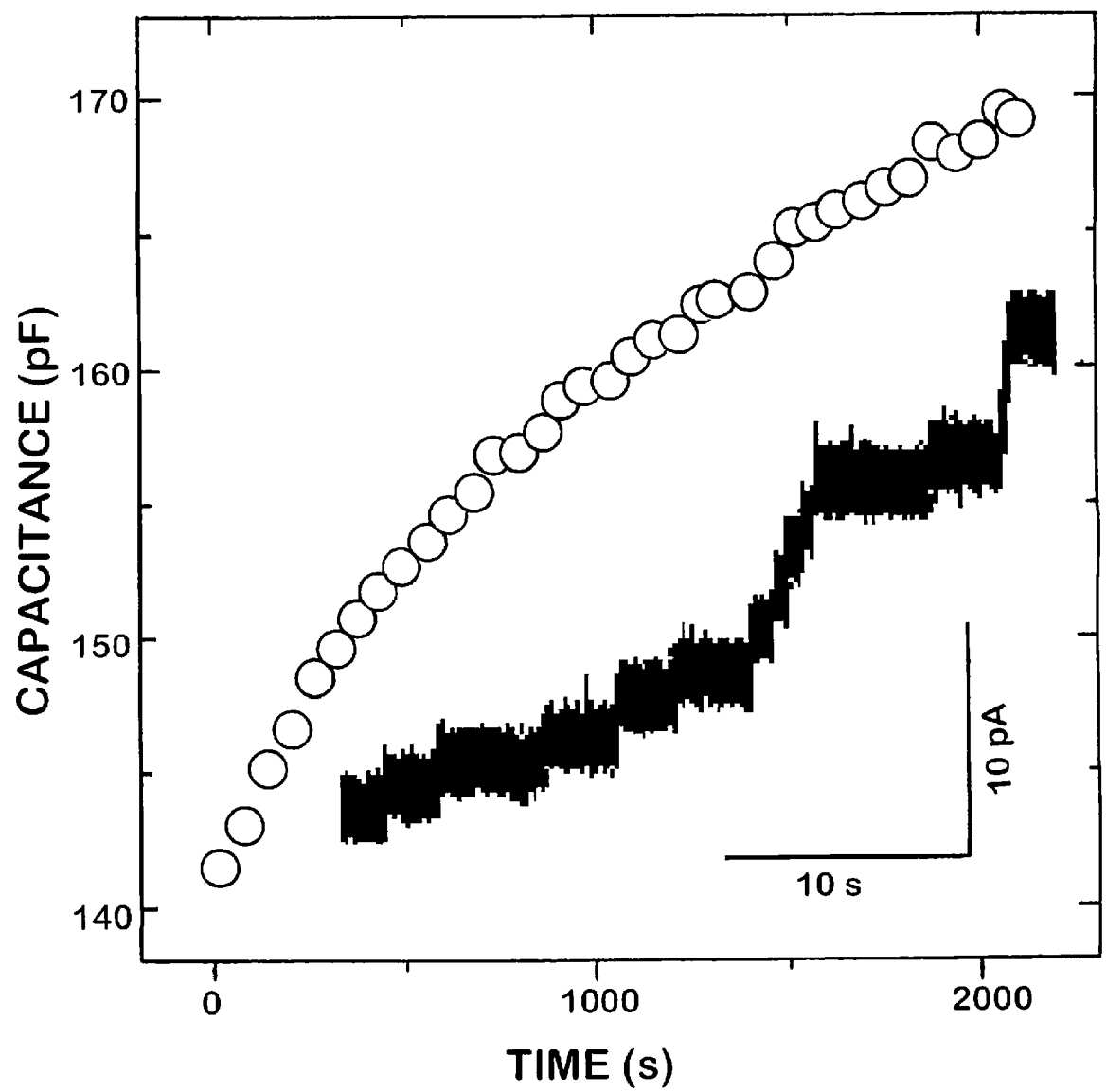
FIG. 8 shows the capacitance of a 1-palmitoyl-2-10,12-tricosadiynoyl-sn-glycero-3-phosphoethanolamine (PTPE) BLM before and after illumination with UV light.

The data in FIG. 8 demonstrates that the capacitance of a PTPE BLM increases (typically between 6% and 40%) upon illumination with UV light. Illumination of the membrane with a pen ray UV lamp for 30 min (50% duty cycle, 30 s on, 30 s off) caused a monotonic increase in the membrane capacitance. The inset demonstrates that even after UV illumination of a PTPE membrane, the pore-forming toxin *Staphylococcus aureus* α-hemolysin caused step increases in the ionic current. Generally, the longer the exposure time, the greater the increase in the membrane capacitance. Control experiments showed that the capacitance of DiPhyPC membranes increased by less than 5% with similar light exposure.

Figure 10:
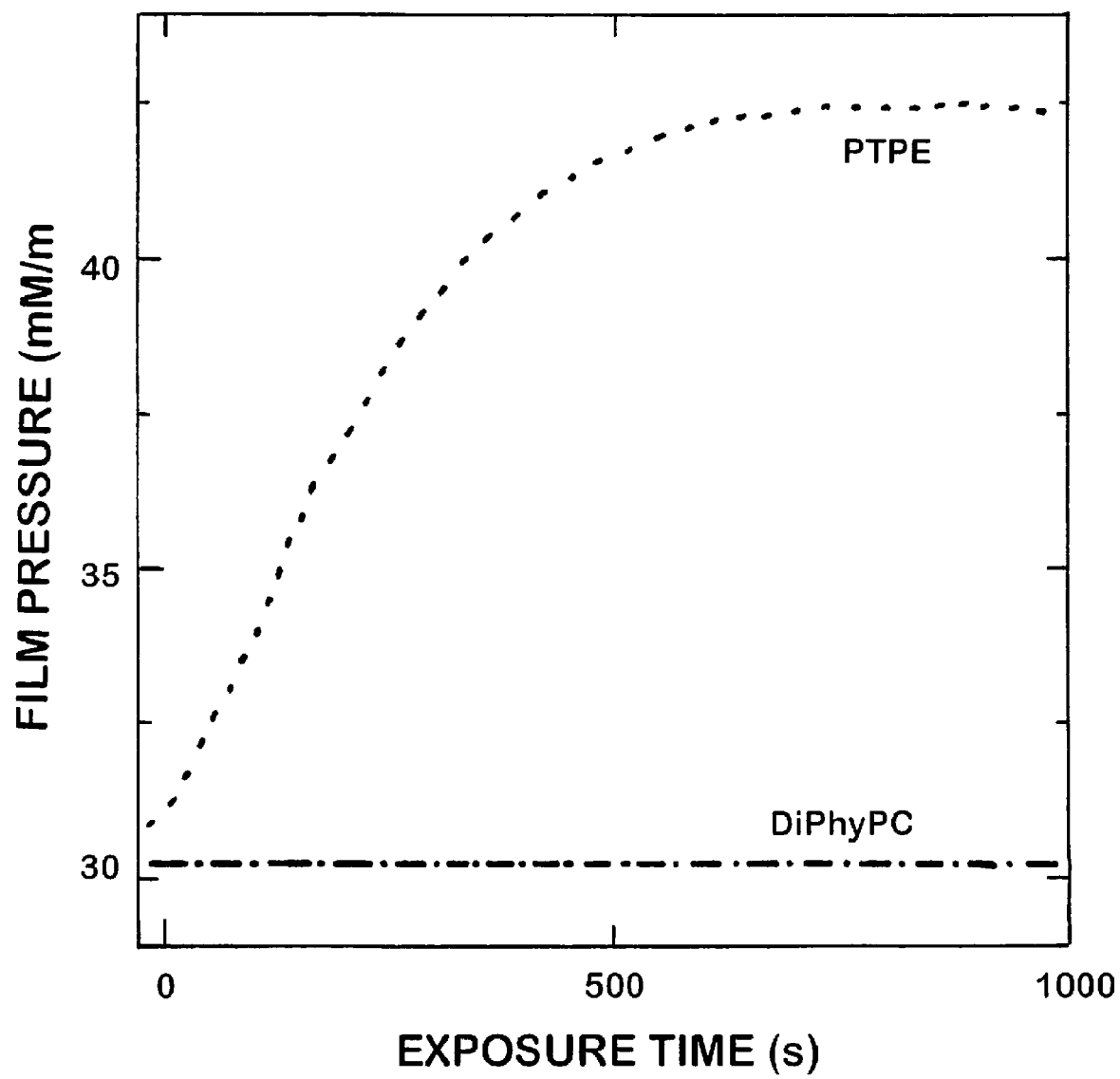
FIG. 10 shows film surface pressure of a compressed monolayer film of PL molecules at the air water interface of an LB trough.
Figure 11:
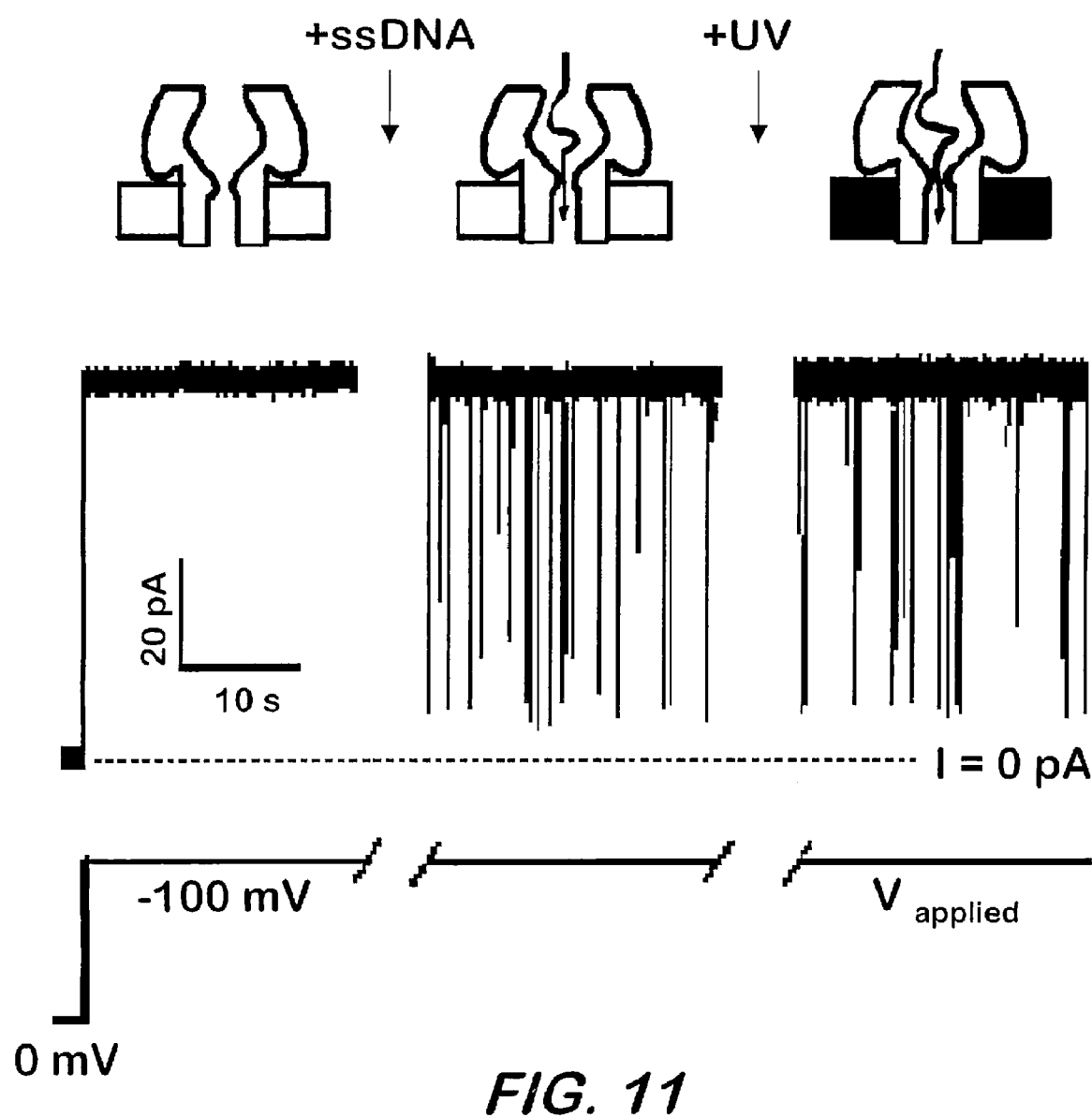
FIG. 11 shows the single channel current that flows through the αHL channel in a PTPE membrane.
Figure 12:
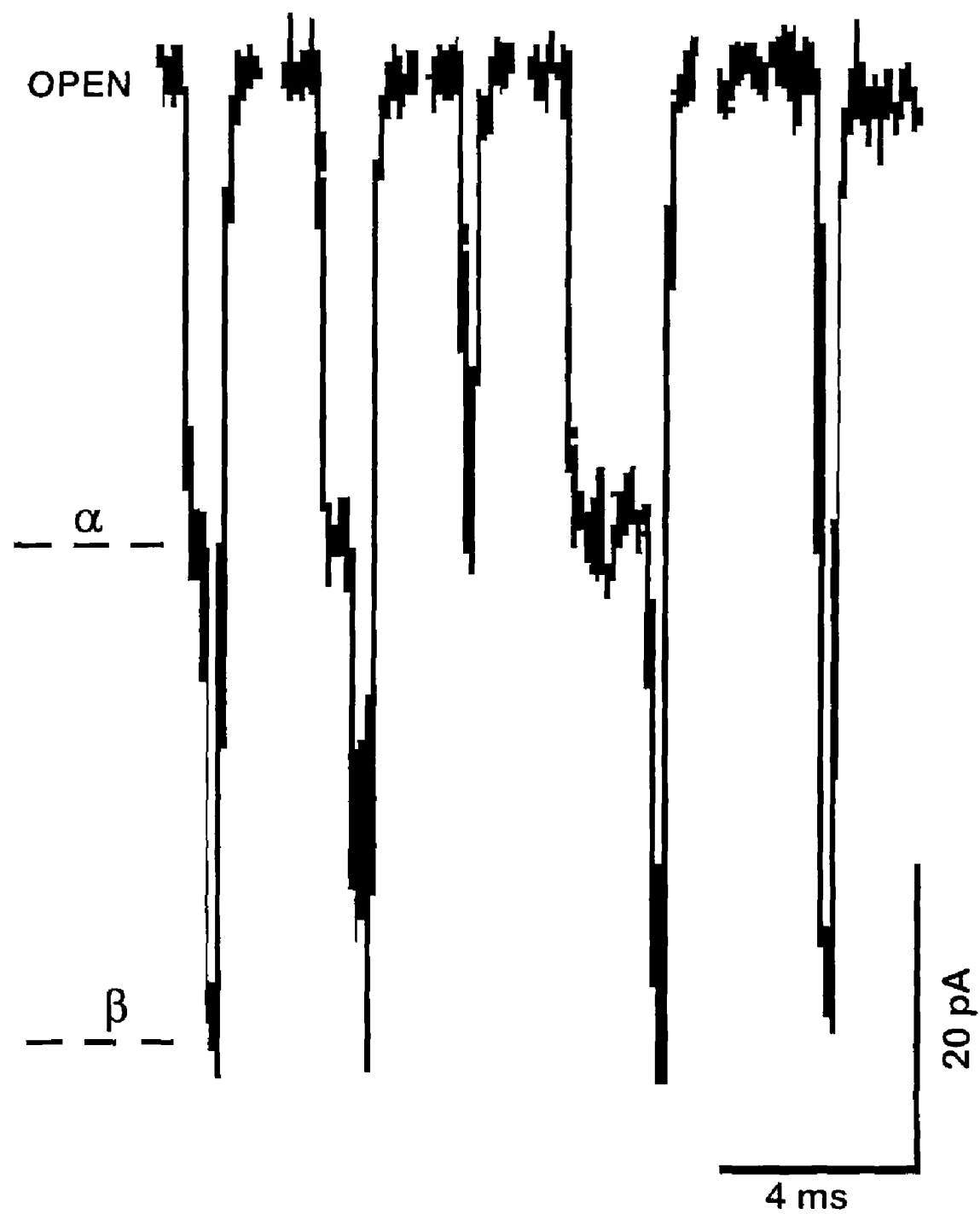
FIG. 12 illustrates the types of blockades caused by poly $[dT]_{50}$ after UV irradiation.
Figure 13:
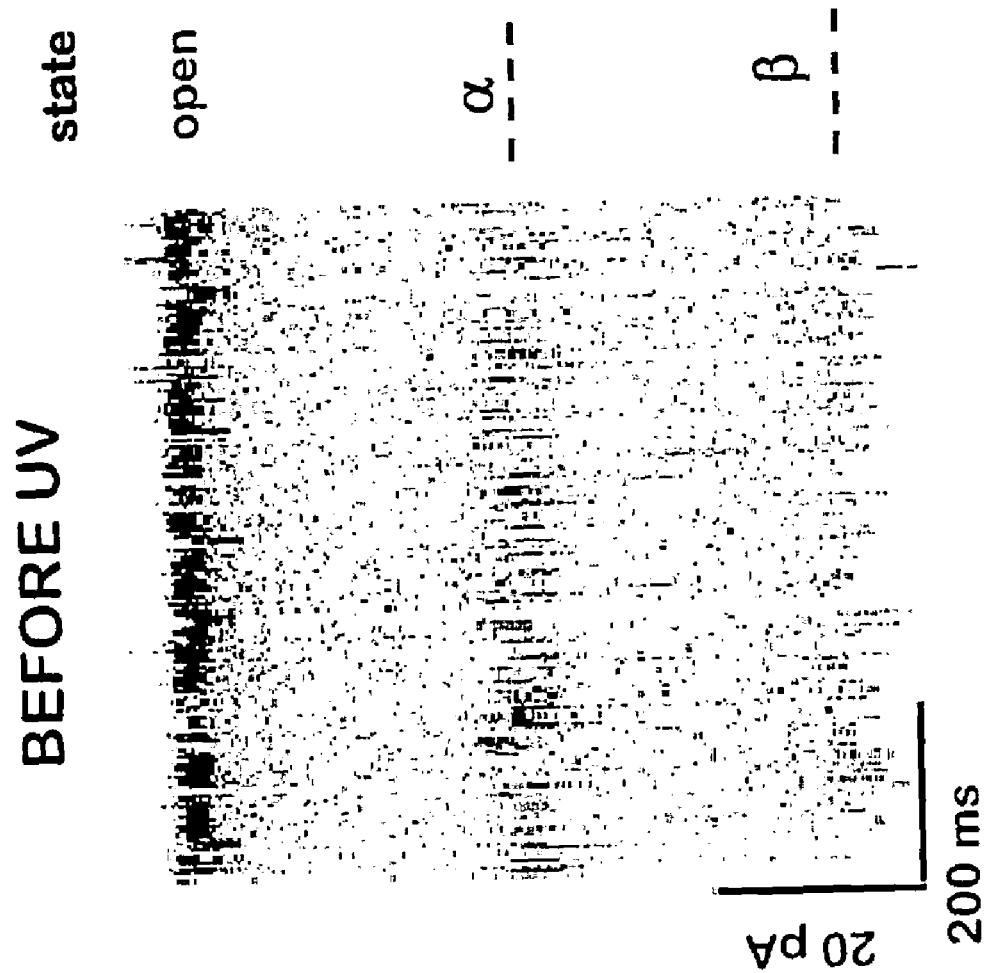
FIG. 13 illustrates a time series for a set of many poly $[dT]_{50}$-induced current blockades before (left) and after (right) UV illumination.

An independent measure of polymerizable phospholipid (PL) polymerization was obtained by monitoring the surface pressure of a compressed monolayer film of PL molecules at the air water interface of an LB trough. FIG. 10 shows an example of this for a PTPE film. A PTPE monolayer was spread at the air-water interface and the subsequently compressed to a film pressure of II ~31 mN/m. At constant barrier separation, the monolayer was then exposed to a constant UV irradiation. The film pressure increased to a limiting value (~42 mN/m) within ~10 min. Control experiments with a monolayer formed from DiPhyPC showed no change in film pressure. FIG. 10 shows that the film surface pressure increases with increasing irradiation until a plateau value is reached. Because the film area is fixed, the increase in surface pressure is due to an increase in the area per lipid molecule. Phospholipid diacetylenic polymerization causes the molecules to tilt thereby increasing both the molecular area and the surface pressure.

EXAMPLE 4

Surface compressional modulus—To determine the elastic modulus (i.e., stiffness) of the insoluble monolayers at the air-water interface, the surface compression modulus was estimated from the LB isotherms using the expression in Eq. (4)

$$M=-d\Pi/d\log_e(A) \tag{4}$$

where II is the surface pressure and A is the area per lipid molecule. Greater values of M correspond to stiffer films. For pure straight-chain fatty acids and other ideally behaving monolayers, II vs. $\log_e(A)$ graphs usually consist of two or more straight-line segments.

Figure 9:
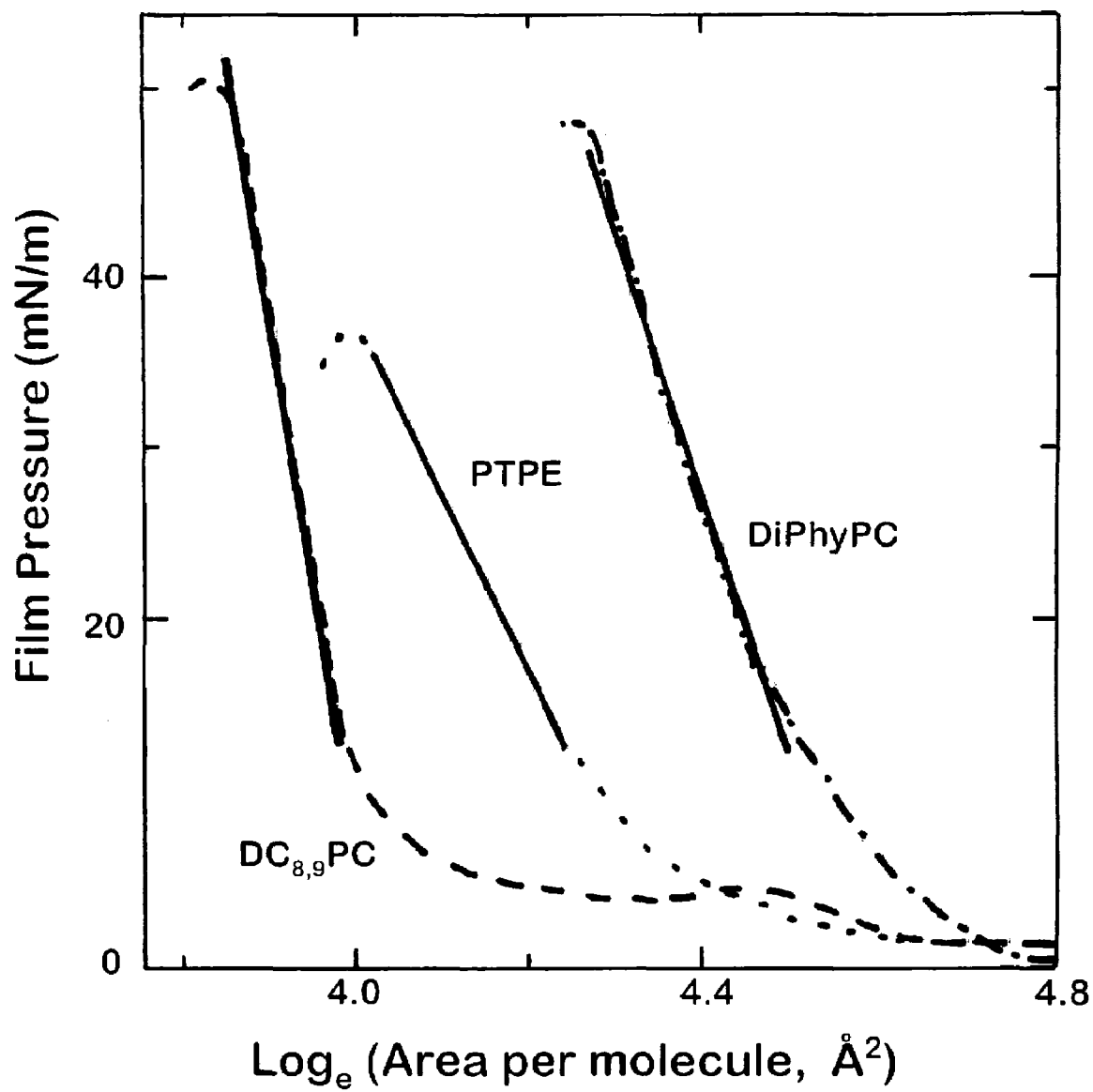
FIG. 9 shows LB isotherms of the lipid monolayers at the air-water interface.

The LB isotherms of the lipid monolayers at the air-water interface are shown in FIG. 9. The solid lines through each of the isotherms are the results of a linear least-square fits of an equation for the surface compressional modulus to the film pressure data. $DC_{8,9}PC$ has a significantly steeper isotherm at high pressures than do PTPE and DiPhyPC. The results suggest that $DC_{8,9}PC$ is approximately 2 and 3 times as stiff as DiPhyPC and PTPE, respectively. The results suggest that $DC_{8,9}PC$ monolayers are more solid-like, whereas the other two lipid monolayers are more liquid crystalline-like. A linear least squares fit of the equation that describes the dependence of the monolayer modulus to the area per lipid molecule to the data between 15 mN/m and 40 mN/m (35 mN/m for PTPE) suggests that the film stiffness follows the sequence $DC_{8,9}PC > DiPhyPC > PTPE$. For comparison, a 24-carbon, straight-chain fatty acids have two characteristic moduli: ~600 mN/m above film pressures of 25 mN/m (upright, solid-like phase) and ~120 mN/m below 25 mN/m (tilted, liquid-like phase).

The different estimated values of the surface compression modulus (i.e., 300 mN/m, 150 mN/m, and 105 mN/m for monolayers of $DC_{8,9}PC$, DiPhyPC and PTPE, respectively)

reflect the differences in the chemical structures of these three lipids. Specifically, $DC_{8,9}PC$ molecules might pack more closely than those of DiPhyPC or PTPE because both of its hydrocarbon tails are identical and can therefore interact relatively strongly through dispersive forces. In contrast, DiPhyPC has methyl groups on every fourth carbon of the two main chains (i.e., it is a branched chain compound) that confer fluidity to the chains. Similarly, PTPE has one chain derived from palmitic acid (a 16-carbon straight acyl chain) and the other chain derived from 11,12-tricosenoic acid (a 23 carbon kinked chain). The second chain, which is identical to either of the two chains of $DC_{8,9}PC$, has a bend in the middle due to the diacetylene group. In both DiPhyPC and PTPE, steric hindrance prevents the close packing of the tails and should therefore form more liquid-like monolayers than would $DC_{8,9}PC$.

EXAMPLE 5

Protein channel formation—Details of the experimental method for reconstituting pore-forming toxins into bilayer membranes are described by Kasianowicz et al., "Protonation dynamics of the α-toxin ion channel from spectral analysis of pH dependent current fluctuations," Biophys. J., 69, 94-105 (1995). For example, following the formation of a PTPE bilayer membrane, ~0.4 µL of 1 mg/mL Bacillus anthracis protective antigen 63 (PA63) was added to one half of the chamber (herein identified as the cis compartment) while stirring. The solution contained 0.1M KCl, 5 mM EDTA, pH6.6. As shown in FIG. 7, the formation of individual ion channels is indicated by characteristic step increases in the ionic current for a fixed value, +50 mV, of the applied potential. The inset in FIG. 7 illustrates the current-voltage relationship for the conductance equivalent of ~50 PA63 channels. The shape of the I-V relationship is nonlinear and rectifying, as was observed for PA63 channels in membranes formed with DiPhyPC.

The pore-forming toxin *Staphylococcus aureus* α-hemolysin (αHL) forms channels from seven identical monomers in liquid crystalline PTPE membranes. Despite the change in the membrane physical state upon UV irradiation, the data in FIG. 8 (inset) demonstrates that αHL forms channels in a polymerized PTPE membrane. Most likely, some lipids in that thin film were still in the liquid-crystalline state. Indeed, in the absence of pore-forming proteins, transient spikes were observed in the ionic current through the membrane after more intense UV illumination. This effect may be caused by a defect (e.g., a geometric mismatch) in the interface between polymerized and non-polymerized lipids.

The ionic current recordings in FIGS. 7 and 8 demonstrate that both *B. anthracis* PA63 and *S. aureus* αHL form ionic channels in PTPE membranes. The stepwise increases in ionic current are consistent with the single channel conductances for o+HL and PA63 in nonpolymerizable lipid membranes.

EXAMPLE 6

Electrophoresis—It has been shown earlier that individual molecules of single stranded RNA and DNA can be driven electrophoretically through a single αHL channel in DiPhyPC BLMs (Kasianowicz et al., "Characterization of individual polynucleotide molecules using a membrane channel," *Proc. Natl. Acad. Sci.* (*USA*), 93, 13770-13773 (1996); Kasianowicz et al., "Simultaneous multianalyte detection with a nanopore," *Analytical Chemistry,* 73, 2268-2272 (2001)). The result in FIG. 11 shows that the single channel current that flows through the αHL channel in a PTPE membrane is relatively large and quiescent (the single channel conductance is virtually indistinguishable from that in DiPhyPC membranes). The subsequent addition of ~40 μL of 50-nucleotide long poly(thymidine) (poly$[dT]_{50}$) to the cis side of the chamber caused short lived blockades and these blockades were present even after irradiating the system with UV light. FIG. 12 illustrates the types of blockades caused by poly$[dT]_{50}$ after UV irradiation (the patterns are virtually identical to those before UV illumination). Notice that there are predominately three conducting states, fully open, partially blocked (state α) and nearly fully blocked (state β). Moreover, some of the blockades have a characteristic two-state pattern that start in state α and then transition to state β. These patterns are characteristic of poly$[dT]_{100}$ entering and threading through the αHL channel in the membranes formed from DiPhyPC. FIG. 13 illustrates a time series for a set of many poly$[dT]_{50}$-induced current blockades before (left) and after (right) UV illumination. In this view of the data, it is clear that the most probable states correspond to those illustrated in FIG. 12. The density of the plot after UV irradiation appears greater because the number of data points is greater.

EXAMPLE 7

$DC_{8,9}PC$—Similar ion channel reconstitution experiments were performed with the polymerizable lipid $DC_{8,9}PC$. Only 2 of 18 attempts to form a membrane were successful, in contrast to a 100% success rate with PTPE bilayer membranes. Also, in one experiment with $DC_{8,9}PC$, the membrane was not stable even for moderate values of the dc applied potentials (i.e., V>100 mV). These issues notwithstanding, αHL was still able to functionally reconstitute into $DC_{8,9}PC$ planar membranes.

EXAMPLE 8

Head group polymerization—A glass slide was silanized in several steps. First, the slide was heated in 40% sulfuric acid, followed by rinsing in an HCl:methanol solution, followed by baking. Then the slide was treated with 1 wt. % silane in toluene, rinsed in 94% methanol/5% water/1% ammonium, and cured at 120° C. DPPE-DVBA was deposited on the slide by dipping into a Langmuir-Blodgett trough under constant pressure. The DPPE-DVBA was polymerized by UV exposure at 254 nm for 2 hr from a distance of 170 mm from the light source.

Obviously, many modifications and variations of the present invention are possible in light of the above teachings. It is therefore to be understood that the claimed invention may be practiced otherwise than as specifically described.

What is claimed is:

1. A structure comprising:

a membrane of a compound spanning an aperture;

wherein the compound comprises a hydrophilic head group and an aliphatic tail group;

wherein the compound comprises a polymerizable or polymerized functional group;

wherein the membrane further comprises an ion channel forming a pore through the membrane; and wherein the ion channel is *Staphylococcus aureus* alpha-hemolysin or *Bacillus anthracis* protective antigen 63.

2. The structure of claim 1, wherein the tail group comprises an ester group.

3. The structure of claim 1, wherein the tail group comprises a $C_{11}$-$C_{24}$ aliphatic.

4. The structure of claim 1, wherein the compound comprises two tail groups.

5. The structure of claim 1;
wherein the membrane is a bilayer membrane;
wherein a majority of the head groups are on the surfaces of the membrane;
wherein a majority of the tail groups are in the interior of the membrane; and
wherein the tail group comprises the functional group.

6. The structure of claim 4;
wherein the compound comprises two tail groups; and
wherein one and only one of the tail groups comprises the functional group.

7. The structure of claim 4, wherein the functional group is a diacetylene group.

8. The structure of claim 4, wherein the functional group is a polymerized diacetylene group.

9. The structure of claim 4, wherein the head group is selected from the group consisting of phosphoethanolamine and phosphocholine.

10. The structure of claim 4, wherein the compound has a surface compressional modulus of from about 50 to about 150 mN/m.

11. The structure of claim 4, wherein the compound is selected from the group consisting of a 1-palmitoyl-2-tricosadiynoyl-glycero-3-phosphoethanolamine having a diacetylene group in the tricosadiynoyl group and a 1-palmitoyl-2-tricosadiynoyl-sn-glycero-3-phosphoethanolamine having a diacetylene group in the tricosadiynoyl group.

12. The structure of claim 4, wherein the compound is selected from the group consisting of 1-palmitoyl-2-10,12-tricosadiynoyl-glycero-3-phosphoethanolamine and 1-palmitoyl-2-10,12-tricosadiynoyl-sn-glycero-3-phosphoethanolamine.

13. The structure of claim 1;
wherein the head group comprises the functional group; and
wherein the membrane is on a solid surface.

14. The structure of claim 13, wherein the head groups are covalently bound to the solid surface.

15. The structure of claim 13, where the head group is phospho-N-(2-hydroxymethyl)-3,5-divinylbenzamide or polymerized phospho-N-(2-hydroxymethyl)-3,5-divinylbenzamide.

16. The structure of claim 13, wherein the compound is 1,2-dipalmitoyl-sn-glycero-3-phospho-N-(2-hydroxymethyl)-3,5-divinylbenzamide.

17. The structure of claim 1, wherein the aperture is from about 2 nm to about 250 microns in diameter.

18. The structure of claim 1, wherein the aperture is from about 10 microns to about 100 microns in diameter.

19. The structure of claim 1, wherein the ion channel is *Staphylococcus aureus* alpha-hemolysin.

20. The structure of claim 1, wherein the ion channel is *Bacillus anthracis* protective antigen 63.

21. A structure comprising:
a bilayer membrane of a compound spanning an aperture;
wherein the compound comprises a hydrophilic head group and two aliphatic tail groups;
wherein one and only one of the tail groups comprises a polymerizable or polymerized functional group; and
wherein the compound is selected from the group consisting of a 1-palmitoyl-2-tricosadiynoyl-glycero-3-phosphoethanolamine having a diacetylene group in the tricosadiynoyl group, a 1-palmitoyl-2-tricosadiynoyl-sn-glycero-3-phosphoethanolamine having a diacetylene group in the tricosadiynoyl group, 1-palmitoyl-2-10,12-tricosadiynoyl-glycero-3-phosphoethanolamine, and 1-palmitoyl-2-10,12-tricosadiynoyl-sn-glycero-3-phosphoethanolamine.

22. The structure of claim 21, wherein the membrane further comprises:
an ion channel forming a pore through the membrane.

23. The structure of claim 22, wherein the ion channel is selected from the group consisting of a protein ion channel, *Staphylococcus aureus* alpha-hemolysin, *Bacillus anthracis* protective antigen 63, gramicidin, and a non-naturally occurring compound.

* * * * *